US012766115B2

(12) United States Patent
Zhu et al.

(10) Patent No.: US 12,766,115 B2
(45) Date of Patent: Oct. 20, 2026

(54) COENZYME Q10 MICROEMULSION, PREPARATION METHOD THEREFOR AND USE THEREOF

(71) Applicants: ZHEJIANG NHU CO., LTD., Zhejiang (CN); ZHEJIANG UNIVERSITY, Zhejiang (CN); XINCHANG NHU VITAMINS COMPANY LTD., Zhejiang (CN); HEILONGJIANG NHU BIOTECHNOLOGY COMPANY LTD., Hei Longjiang (CN)

(72) Inventors: Xiaoyong Zhu, Zhejiang (CN); Jiandong Li, Zhejiang (CN); Hongyue Yan, Zhejiang (CN); Zhirong Chen, Zhejiang (CN); Jincheng Cheng, Zhejiang (CN); Qilei Zhang, Zhejiang (CN); Wei Li, Zhejiang (CN); Tianqi Lv, Hei Longjiang (CN); Guilai Wang, Zhejiang (CN)

(73) Assignees: ZHEJIANG NHU CO. LTD., Zhejiang (CN); ZHEJIANG UNIVERSITY, Zhejiang (CN); XINCHANG NHU VITAMINS COMPANY LIMITED, Zhejiang (CN); HEIJONGJIANG NHU BIOTECHNOLOGY COMPANY LTD., Hej Longjiang (CN)

( * ) Notice: Subject to any disclaimer, the term of this patent is extended or adjusted under 35 U.S.C. 154(b) by 365 days.

(21) Appl. No.: 18/256,231

(22) PCT Filed: Mar. 24, 2022

(86) PCT No.: PCT/CN2022/082838

§ 371 (c)(1),
(2) Date: Jun. 7, 2023

(87) PCT Pub. No.: WO2022/222683

PCT Pub. Date: Oct. 27, 2022

(65) Prior Publication Data

US 2024/0016763 A1 Jan. 18, 2024

(30) Foreign Application Priority Data

Apr. 23, 2021 (CN) ........................ 202110441892.9

(51) Int. Cl.

| | |
|---|---|
| ***A61K 31/122*** | (2006.01) |
| ***A23L 2/52*** | (2006.01) |
| ***A23L 29/00*** | (2016.01) |
| ***A23L 33/10*** | (2016.01) |
| ***A61K 8/06*** | (2006.01) |
| ***A61K 8/35*** | (2006.01) |

(Continued)

(52) U.S. Cl.

CPC .............. *A61K 31/122* (2013.01); *A23L 2/52* (2013.01); *A23L 29/06* (2016.08); *A23L 33/10* (2016.08); *A61K 8/068* (2013.01); *A61K 8/355* (2013.01); *A61K 8/922* (2013.01); *A61K 47/24* (2013.01); *A61K 47/44* (2013.01); *A61Q 19/00* (2013.01); *A61K 2800/10* (2013.01)

(58) Field of Classification Search

CPC ...... A61K 31/122; A61K 8/068; A61K 8/355; A61K 8/922; A61K 47/24; A61K 47/44; A61K 2800/10; A61K 8/375; A61K 8/678; A61K 8/8176; A61K 8/86; A61K 9/0095; A61K 9/1075; A61K 47/10; A61K 47/14; A61K 47/22; A23L 2/52; A23L 29/06; A23L 33/10; A61Q 19/00

See application file for complete search history.

(56) References Cited

U.S. PATENT DOCUMENTS

2006/0134085 A1 6/2006 Yamaguchi
2006/0275358 A1* 12/2006 Lin

FOREIGN PATENT DOCUMENTS

CN 101015524 A 8/2007
CN 101744288 A 6/2010

(Continued)

OTHER PUBLICATIONS

International Search Report issued in corresponding International PCT Application No. PCT/CN2022/082838; Mailing Date: Jun. 27, 2022.

*Primary Examiner* — Robert A Wax
*Assistant Examiner* — Kimberly Barber
(74) *Attorney, Agent, or Firm* — Chrisman Gallo Tochtrop LLC

(57) ABSTRACT

Provided in the present invention are a coenzyme Q10 microemulsion, a preparation method therefor and the use thereof. The coenzyme Q10 microemulsion is prepared from components comprising coenzyme Q10, a carrier oil, an anti-crystallization agent, a lipophilic emulsifier, a hydrophilic emulsifier, a co-emulsifier and water. The microemulsion has a particle size $D_V(90)$ of between 20 nm and 80 nm, and is clear, transparent, free of demulsification and high in bioavailability, can be stably stored for a long time at normal temperatures and in extreme temperature environments. In addition, the microemulsion is suitable for the pharmaceutical, cosmetic and food fields, especially for beverages, oral liquids and other products. Also provided in the present invention is a method for preparing the coenzyme Q10 microemulsion, which is simple in equipment, low in cost and easy in operation.

6 Claims, 2 Drawing Sheets

(51) Int. Cl.

| | |
|---|---|
| ***A61K 8/92*** | (2006.01) |
| ***A61K 47/24*** | (2006.01) |
| ***A61K 47/44*** | (2017.01) |
| ***A61Q 19/00*** | (2006.01) |

(56) References Cited

FOREIGN PATENT DOCUMENTS

| | | | |
|---|---|---|---|
| CN | 102423297 | A | 4/2012 |
| CN | 106727441 | A | 5/2017 |
| CN | 107568731 | A | 1/2018 |
| CN | 113509437 | A | 10/2021 |
| WO | WO2009022798 | A2 * | 2/2009 |

* cited by examiner

COENZYME Q10 MICROEMULSION, PREPARATION METHOD THEREFOR AND USE THEREOF

TECHNICAL FIELD

The present disclosure relates to a coenzyme Q10 microemulsion having small particle size, long-term storage stability in extreme temperature environments and high bioavailability, and to a preparation method therefor and use thereof. More specifically, the present disclosure relates to the use of coenzyme Q10 microemulsion in beverages or oral liquids.

BACKGROUND

In the prior art, there are many researches on the preparation methods and uses of microemulsion. For example, coenzyme Q10 oral emulsions for pharmaceuticals, coenzyme Q10 nano-microcapsule emulsions for cosmetics, coenzyme Q10 clear oral formulations for food additives all involve microemulsion.

Patent Document 1 discloses a self-microemulsion and a preparation method therefor, wherein the formula for preparing coenzyme Q10 self-microemulsion is approximately as follows: 5% to 20% of coenzyme Q10, 5% to 20% of caprylic/capric triglyceride, 1% to 5% of Span 60, 15% to 25% of Tween 60, 1% to 5% of sodium stearate, 20% to 30% of glycerol, 1% to 2% of sorbitol and 8% to 15% of water. The preparation method is as follows: coenzyme Q10 is added into caprylic/capric triglyceride, then an emulsifier Span 60 is added, nitrogen is supplemented for three times after vacuumizing in the dark, followed by heating and stirring until the solid materials are completely dissolved; then a certain amount of an co-emulsifier glycerol is added, and then primary emulsifiers Tween 60 and sodium stearate are added; sorbitol is dissolved in pure water and finally is added into the mixed system, which is heated at about 65° C. in the dark and under oxygen isolation whiling being stirred until the system becomes uniform and transparent, then the system is kept warm for 10 minutes to 30 minutes and then cooled to get the final product. The self-microemulsion product can be stably stored at the temperature of −10° C. to 60° C., but the stability at low temperature (−30° C. to −10° C.) and high temperature (100° C. to 130° C.) is not involved.

Patent Document 2 discloses a clear oral formulation containing coenzyme Q10 and a preparation method therefor. The formula for preparing the oral formulation is approximately as follows: 0.1% to 10% of coenzyme Q10, 0.5% to 30% of an emulsifier, 5% to 20% of a co-emulsifier, 0.5% to 10% of a stabilizer and the balance of water. The preparation method therefor is as follows: the respective raw materials are weighed according to the formula, and coenzyme Q10 is firstly dissolved in the emulsifier and co-emulsifier, and then the mixture is added into water containing the stabilizer to form a uniform mixed solution, followed by high-speed shearing to prepare the final solution. The method does not use an organic solvent, requires simple equipment, and can prepare a uniform nano-dispersion system of coenzyme Q10 having a clear appearance, which has good dispersibility and can improve bioavailability, and the coenzyme Q10 aqueous solution can be stored stably for one year or more. However, this invention only gives stability date of coenzyme Q10 microemulsion at 25° C., and does not address the stability situation at low temperature (−30° C. to −10° C.) and high temperature (100° C. to 130° C.). Coenzyme Q10 microemulsion needs to undergo extreme temperature environments such as high-temperature sterilization and refrigerated storage in subsequent uses such as oral liquid, beverage, soft capsule, food, etc., but the microemulsion in the prior art at present is not stable enough in the above extreme temperature environments and is prone to demulsify, which leads to the destruction of its activities. Therefore, the performance and preparation process of current coenzyme Q10 microemulsion still need to be improved.

Patent Document 3 discloses a coenzyme Q10 oral emulsion and preparation method therefor. The components of the coenzyme Q10 oral emulsion and the contents thereof are as follows: 0.1% to 80% of coenzyme Q10, 1% to 95% of a medicinal oil, 0.5% to 30% of an emulsifier, 0% to 10% of a co-emulsifier, 0.001% to 15% of an antioxidant and the balance of purified water. The preparation is carried out by methods such as phase inversion emulsification, PIT emulsification, alternate liquid addition emulsification, continuous emulsification, low energy emulsification and microfluidization. After undergoing centrifugation for 30 minutes at a rotating speed of 3750 r/min, the prepared oral emulsion has no stratification phenomenon, has high bioavailability and good stability, so it is easier to be taken by patients. However, this invention does not involve the stability of coenzyme Q10 oral emulsion at normal temperature, low temperature (−30° C. to −10° C.) and high temperature (100° C. to 130° C.).

Patent Document 4 discloses a coenzyme Q10 fish oil nano-emulsion and a preparation method therefor as well as use thereof. The components of the coenzyme Q10 fish oil nano-emulsion and the contents thereof are as follows: 0.02% to 25% of coenzyme Q 100, 0% to 20% of a fish oil, 0.5% to 5% of an emulsifier, 0% to 20% of a vegetable oil, 0% to 10% of a correctant, 0% to 0.5% of an antioxidant, 0% to 0.5% of a preservative, proper amount of a pH regulator and proper amount of purified water. In the preparation process of the coenzyme Q10 fish oil nano-emulsion, operations such as shearing and high-pressure homogenization are adopted, and the obtained emulsion has a particle size of 300 nm to 550 nm, which does not involve the stability of the coenzyme Q10 fish oil nano-emulsion at normal temperature, low temperature (−30° C. to −10° C.) and high temperature (100° C. to 130° C.).

PRIOR ART DOCUMENTS

Patent Document 1: CN102423297B
Patent Document 2: CN101744288B
Patent Document 3: CN101015524A
Patent Document 4: CN107568731A

SUMMARY

Technical Problem

To overcome the shortcoming of coenzyme Q10 microemulsion in the prior art, such as insufficient stability in extreme temperature environments (e.g., at low temperature (−30° C. to −10° C.) and high temperature (100° C. to 130° C.)), the present disclosure hopes to develop a coenzyme Q10 microemulsion which has a small particle size and improved extreme temperature stability, the preparation process therefor is simple, and the above-mentioned object can be achieved even without technical means such as high-speed shearing, homogenization, ultrasound.

According to the present disclosure, it is further desired that the microemulsion obtained by the above method has the characteristics of high clarity and transparency, large microemulsion area, remaining clear and translucent after being diluted into oral liquid and undergoing high-temperature sterilization, and high bioavailability, and that the coenzyme Q10 still exists in the form of microemulsion when used in food.

Solution to Problem

According to the present disclosure, coenzyme Q10 is first dissolved in a carrier oil, then compounded with specific lipophilic and hydrophilic emulsifiers and kept at a specific temperature, and an emulsified oil-water system is finally formed, to obtain a thermodynamically stable coenzyme Q10 microemulsion.

The present disclosure mainly comprises the following aspects.

[1] A coenzyme Q10 microemulsion comprising, based on a total amount of the coenzyme Q10 microemulsion.

1% to 20% by mass of coenzyme Q10, 1% to 20% by mass of a carrier oil, 0.5% to 10% by mass of an anti-crystallization agent, 2% to 15% by mass of a lipophilic emulsifier, 15% to 30% by mass of a hydrophilic emulsifier, 5% to 25% by mass of a co-emulsifier, and 30% to 65% by mass of water, said coenzyme Q10 microemulsion having a particle size $D_V(90)$ of 20 nm to 80 nm.

[2] The coenzyme Q10 microemulsion according to [1], wherein the lipophilic emulsifier includes polyglycerol ricinoleate.

[3] The coenzyme Q10 microemulsion according to [1] or [2], wherein the hydrophilic emulsifier includes a polyoxyethylene ether-based emulsifier.

[4] The coenzyme Q10 microemulsion according to any one of [1] to [3], wherein the carrier oil is at least one selected from the group consisting of caprylic/capric triglyceride, diethylene glycol monoethyl ether, glycerol polyether, soybean phospholipid and olive oil.

[5] The coenzyme Q10 microemulsion according to [3] or [4], wherein the polyoxyethylene ether-based emulsifier is at least one selected from the group consisting of polyoxyethylene sorbitan oleate, polyoxyethylene sorbitan stearate, polyoxyethylene sorbitan laurate and polyoxyethylene hydrogenated castor oil.

[6] The coenzyme Q10 microemulsion according to any one of [1] to [5], wherein the co-emulsifier is at least one selected from the group consisting of glycerol, sorbitol, ethanol, polyethylene glycol-400 and polyethylene glycol-800.

[7] The coenzyme Q10 microemulsion according to any one of [1] to [6], wherein the anti-crystallization agent is at least one selected from the group consisting of tocopherol acetate, tocopherol, trihydroxystearin, medium-chain triglyceride, povidone K30, povidone K12 and polyglycerol fatty acid ester.

[8] A method for preparing the coenzyme Q10 microemulsion according to any one of [1] to [7], comprising steps of:

forming an oil phase using a coenzyme Q10, a carrier oil and an anti-crystallization agent;

adding a lipophilic emulsifier and a hydrophilic emulsifier into the oil phase;

further adding a co-emulsifier after the oil phase is uniformly mixed, stirring and mixing uniformly, and then adding water dropwise, followed by stirring until the whole system becomes uniform and transparent, keeping the temperature at 90° C. to 120° C. for 0.5 hour to 1 hour, thereby obtaining the coenzyme Q10 microemulsion.

[9] Use of the coenzyme Q10 microemulsion according to any one of [1] to [7] in the preparation of pharmaceuticals, cosmetics and food.

[10] The use according to [9], wherein the use is preparing a beverage or an oral liquid.

Effects

According to the present disclosure, a specific emulsifier is compounded, and the components are mixed and then kept at a specific temperature, so that a coenzyme Q10 microemulsion can be obtained, which has a particle size $D_V(90)$ between 20 nm and 80 nm, is clear and transparent and free of demulsification, has high bioavailability, and has a long-term storage stability in normal temperature and extreme temperature environments (e.g., at low temperature (−30° C. to −10° C.) and high temperature (100° C. to 130° C.)). The microemulsion has a large microemulsion area and can remain in microemulsion form after being diluted 100 times in an aqueous solution, so it is suitable for the pharmaceutical, cosmetic and food fields, especially for products such as beverages and oral liquids. Where the microemulsion is used for beverages and oral liquids, it is not demulsified even after high-temperature sterilization and remains clear and transparent.

In addition, the method according to the present disclosure is simple in process and low in cost, and a coenzyme Q10 microemulsion having a particle size of less than 100 nm can be prepared even without technical means such as high-speed shearing, homogenization, ultrasound.

DETAILED DESCRIPTION

Figure 1:
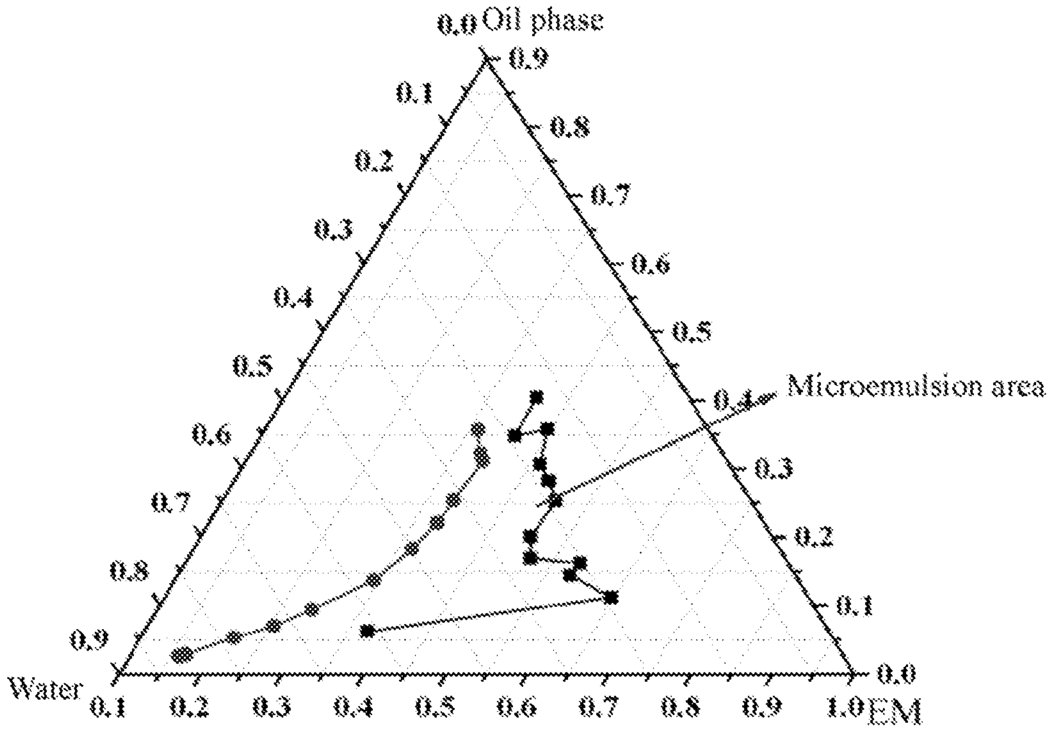
FIG. 1 to FIG. 4 are ternary phase diagrams of the microemulsion areas in the microemulsion systems represented by Example 1, Comparative Example 1, Comparative Example 2 and Comparative Example 3, respectively, wherein EM comprises emulsifiers (including a lipophilic emulsifier, a hydrophilic emulsifier) and a co-emulsifier.
Figure 2:
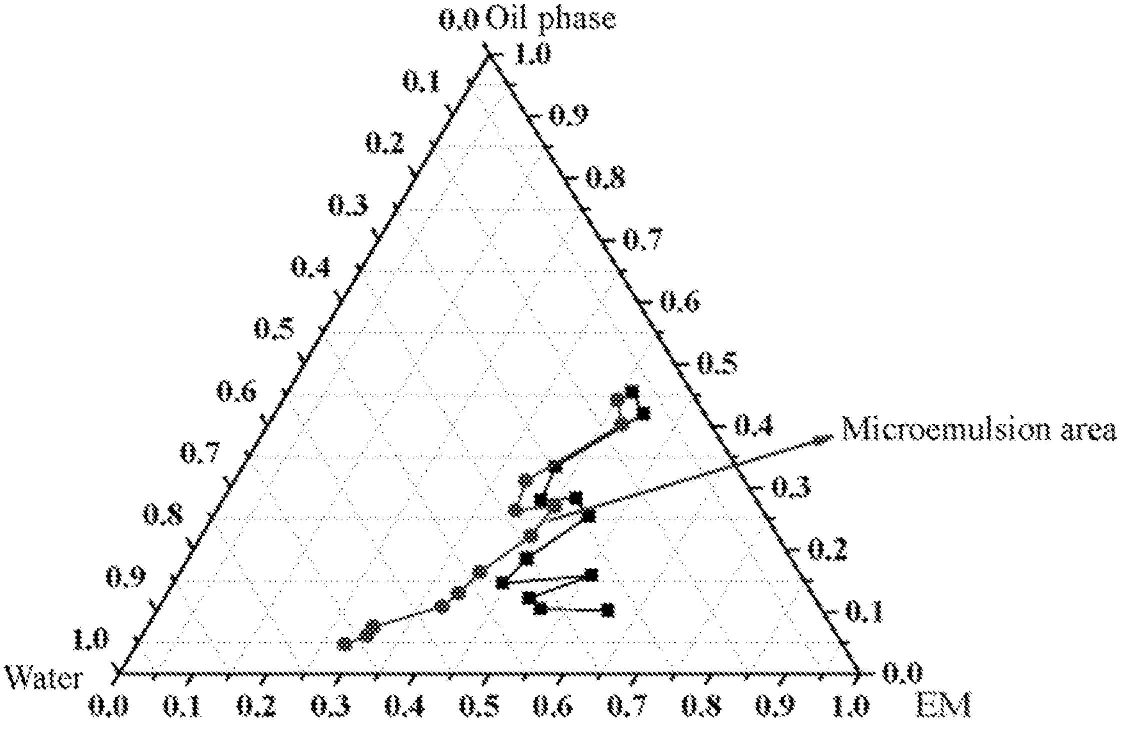
Figure 3:
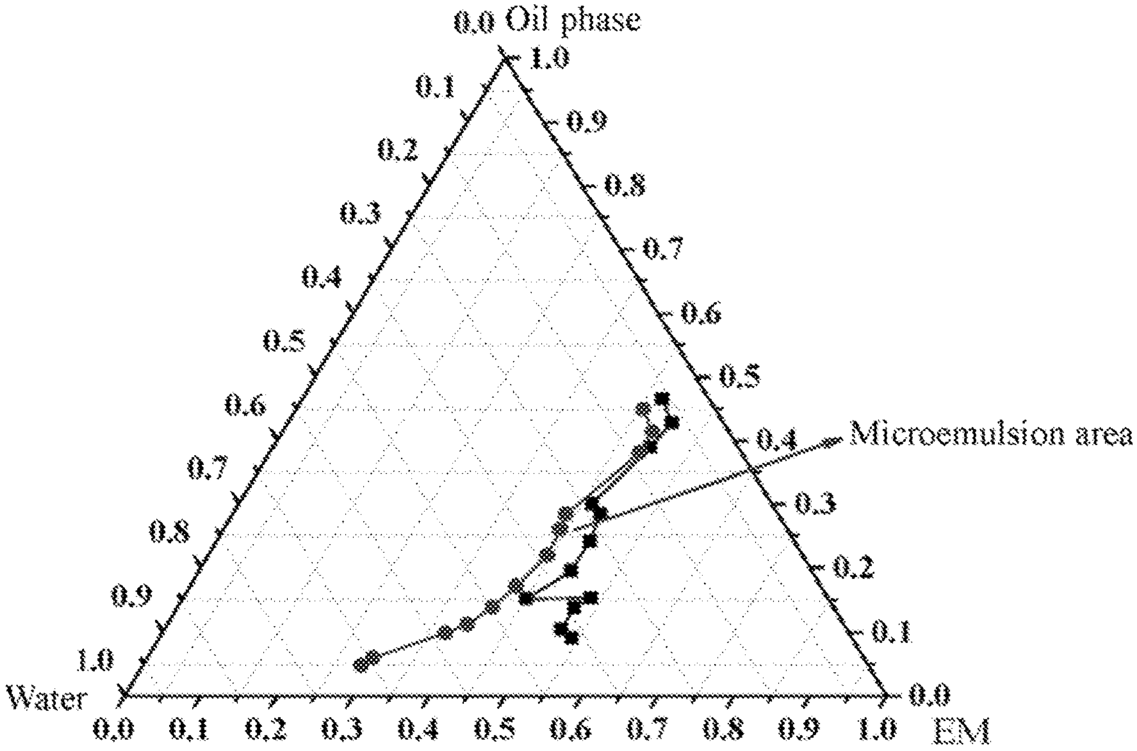
Figure 4:
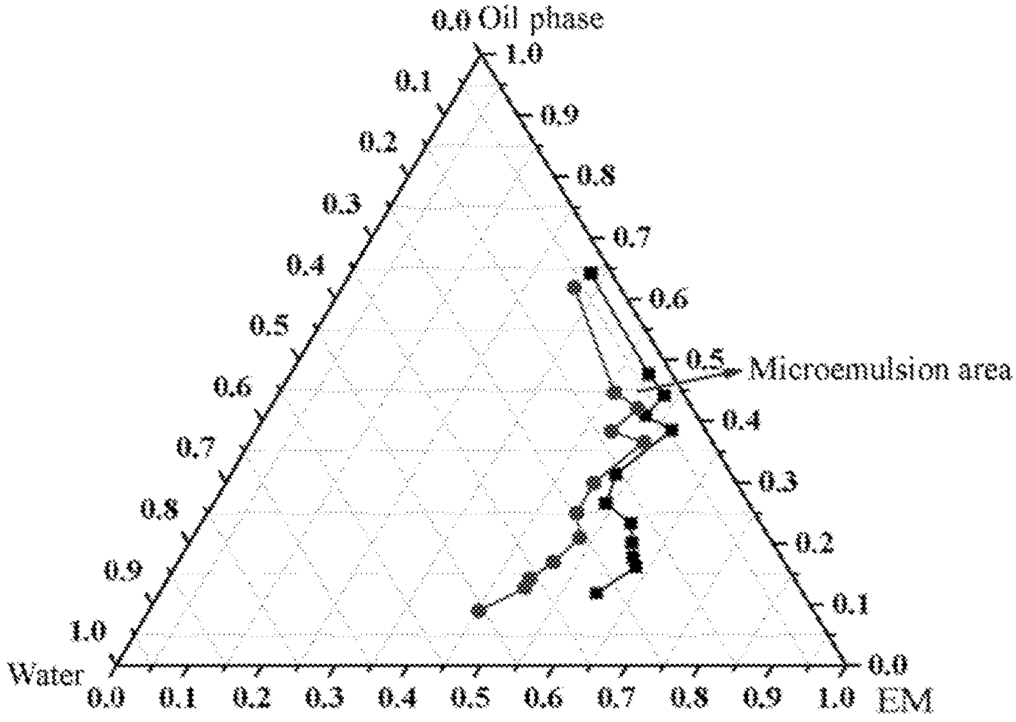

The following is a detailed description of the characteristics, formula, preparation method and use of the coenzyme Q10 microemulsion according to the present disclosure.

<Characteristics of the Coenzyme Q10 Microemulsion According to the Present Disclosure>

In the present disclosure, the emulsifying capacity is improved by a specific lipophilic emulsifier and hydrophilic emulsifier compounding technology, and there is provided a method of preparing microemulsion having high stability and high coenzyme Q10 content.

After research, it is found by the present inventors that when specific lipophilic and hydrophilic emulsifiers are used for compounding, first, the emulsifier system will be adsorbed on the oil-water interface to form a unique emulsifier complex, which is closely and orderly in structure and has high strength, which can well prevent the oil phase from aggregation. Next, when the two specific structures of emulsifiers have hydrophilic groups of different conformations, there is a complementary effect of hydrophilic group conformations (for example, the hydrophilic group of monoglyceride is linear while the hydrophilic group of sucrose fatty acid ester is cyclic), which can effectively disrupt the oriented arrangement of emulsifier molecules and increase stability of the microemulsion. Besides, after the specific lipophilic emulsifier and hydrophilic emulsifier are compounded, the optimal HLB range in the system is expanded, which is no longer a single point.

It is further found by the present inventors that the formation of the aforesaid microemulsion has the following characteristics. Highly soluble triglyceride wraps the crystals of coenzyme Q10 and forms an oil suspension under the action of an oil phase stabilizer (an anti-crystallization agent). Specific lipophilic and hydrophilic emulsifiers are added for compounding, wherein the head group of the lipophilic emulsifier is close to the oil suspension, and the lipophilic group of the emulsifier is embedded with the side chain of Q10 to form a spherical stable arrangement and adhere to the oil suspension. One end of the hydrophilic emulsifier is tightly combined with a branched chain of the lipophilic emulsifier to play a "bridge" role. After pure water is added, the branched chain at the other end of the hydrophilic emulsifier and water molecules adsorb each other, and the water molecules wraps around the periphery of the emulsifier, finally forming an O/W microemulsion.

<Formula>

Properties such as stability and bioavailability of microemulsion are affected by the interaction between the components, and the type and ratio of compounds affect the interaction between the components. After research, it is found by the present inventors that compounds having the following characteristics can be used in the present disclosure, and the desired coenzyme Q10 microemulsion can be obtained after compounding.

The raw material coenzyme Q10 used in the present disclosure may be oxidized, reduced or be a mixture of both as necessary, and said coenzyme Q10 may be obtained by any method, for example, organic synthesis or microbial fermentation. In the formula, the content of coenzyme Q10 is preferably 1% to 20% by mass based on the total amount of the coenzyme Q10 microemulsion. More preferably, the content of coenzyme Q10 is 1% to 15% by mass. Most preferably, the content of coenzyme Q10 is 1% to 10% by mass.

In the present disclosure, a conventional carrier oil in the art can be used as the carrier oil as long as it can dissolve coenzyme Q10 to form an oil phase. From the viewpoint of forming a stable and uniform mixed oil phase and preventing a decrease in the oxidation resistance of coenzyme Q10, the carrier oil is preferably selected from at least one of the group consisting of caprylic/capric triglyceride, diethylene glycol monoethyl ether, glycerol polyether, soybean phospholipid and olive oil. Based on the total amount of the coenzyme Q10 microemulsion, the content of the carrier oil is preferably 1% to 20% by mass. More preferably, the content of the carrier oil is preferably 2% to 10% by mass.

In the present disclosure, the lipophilic emulsifier is polyglycerol ricinoleate from the viewpoint that it is liable to adsorb on the oil-water interface upon compounding to form an emulsifier complex, and that the complex is tightly and orderly arranged and has high strength to prevent the oil phase from aggregation. From the viewpoint that it is helpful to form microemulsion which has a particle size $D_V(90)$ of less than 100 nm, is clear and transparent and free of demulsification, has high bioavailability, and has excellent stability in extreme temperature environments, the content of polyglycerol ricinoleate is preferably 2% to 15% by mass based on the total amount of the coenzyme Q10 microemulsion. More preferably, the content of the lipophilic emulsifier is 5% to 10% by mass.

In the present disclosure, the hydrophilic emulsifier is polyoxyethylene ether-based emulsifier. From the viewpoint that it is liable to adsorb on the oil-water interface upon compounding to form an emulsifier complex, and that the complex is tightly and orderly arranged and has high strength to prevent the oil phase from aggregation, the polyoxyethylene ether-based emulsifier is preferably at least one selected from the group consisting of polyoxyethylene sorbitan oleate (Tween-80), polyoxyethylene sorbitan stearate (Tween-60), polyoxyethylene sorbitan laurate (Tween-20) and polyoxyethylene hydrogenated castor oil. From the viewpoint that it is helpful to form microemulsion which has a particle size $D_V(90)$ of less than 100 nm, is clear and transparent and free of demulsification, has high bioavailability, and has excellent stability in extreme temperature environments, the content of the hydrophilic emulsifier is 15% to 30% by mass based on the total amount of the coenzyme Q10 microemulsion. More preferably, the content of the hydrophilic emulsifier is 17% to 24% by mass.

In the present disclosure, the co-emulsifier is not limited, and any conventional co-emulsifier in the art can be used as long as it can be used in combination with the emulsifiers to help form coenzyme Q10 microemulsion. From the viewpoint of being well mixed with the mixed oil phase and emulsifier system to form a stable and uniform microemulsion, the co-emulsifier is preferably at least one selected from the group consisting of glycerol, sorbitol, ethanol, polyethylene glycol-400 (PEG-400) and polyethylene glycol-800 (PEG-800). More preferably, the co-emulsifier is glycerol and/or sorbitol. From the viewpoint that it is helpful to form microemulsion which has a particle size $D_V(90)$ of less than 100 nm, is clear and transparent and free of demulsification, and has excellent stability in extreme temperature environments, the content of the co-emulsifier is preferably 5% to 25% by mass based on the total amount of the coenzyme Q10 microemulsion. More preferably, the content of the co-emulsifier is 7% to 12% by mass.

In the present disclosure, the anti-crystallization agent is not limited, and any conventional anti-crystallization agent in the art can be used as long as it can be used in combination with the emulsifiers and the co-emulsifier to help form stable coenzyme Q10 microemulsion. From the viewpoint of improving the stability of the microemulsion so that coenzyme Q10 does not crystallize and precipitate over a wide temperature range (above 0° C.), facilitating human absorption and improving bioavailability, the anti-crystallization agent preferably is at least one selected from the group consisting of tocopheryl acetate, tocopherol, trihydroxystearin, medium chain triglyceride, povidone K30, povidone K12, polyglycerol fatty acid ester (THL-17) (purchased from Sakamoto Pharmaceuticals, Japan), and polyglycerol fatty acid ester (THL-15) (purchased from Sakamoto Pharmaceuticals, Japan). From the viewpoint of better reducing the crystallization and precipitation of coenzyme Q10 and improving the stability of the microemulsion, the content of the anti-crystallization agent is preferably 0.5% to 10% by mass, and more preferably, the content of the anti-crystallization agent is 2% to 5% by mass, based on the total amount of the coenzyme Q10 microemulsion.

In the present disclosure, the coenzyme Q10 microemulsion has a particle size $D_V(90)$ of less than 100 nm, and the small particle size is helpful to form a uniform and clear microemulsion, and improve transparency and bioavailability. Preferably, the particle size $D_V(90)$ is within a range of 20 nm to 80 nm, which can make the coenzyme Q10 microemulsion more clear and transparent, free of demulsification, and has excellent stability in extreme temperature environments. More preferably, the particle size $D_V(90)$ is within a range of 30 nm to 75 nm, which can make the coenzyme Q10 microemulsion have better stability and bioavailability in extreme temperature environments. Most preferably, the particle size $D_V(90)$ is within a range of 35 nm to 60 nm, in which case the aforesaid performance of coenzyme Q10 microemulsion is more excellent.

<Preparation Method for the Coenzyme Q10 Microemulsion>

The preparation of the coenzyme Q10 microemulsion of the present disclosure comprises the following steps:

1) forming an oil phase using a coenzyme Q10, a carrier oil and an anti-crystallization agent;

preferably, the coenzyme Q10, carrier oil and anti-crystallization agent are stirred to dissolve in a water bath at 40° C. to 70° C. for 5 to 10 minutes, to form the oil phase;

2) adding a lipophilic emulsifier and a hydrophilic emulsifier into the oil phase; preferably, after each emulsifier is added, magnetic stirring is carried out for 5 to 10 minutes;

3) further adding a co-emulsifier after the oil phase is uniformly mixed, stirring and mixing uniformly, and then adding water dropwise, followed by stirring until the whole system becomes uniform and transparent, keeping the temperature at 90° C. to 120° C. for 0.5 to 1 hour, to obtain the coenzyme Q10 microemulsion.

It is found by the present disclosure that it is particularly important for the stability of the microemulsion to keep the mixture at 90° C. to 120° C. for 0.5 to 1 hour after all the components are added. The heat preservation process of the microemulsion is a process of re-emulsification and aging of the emulsifier, and the selection of appropriate heat preservation conditions is favorable to the formation of sol particles with uniform particle size, which can make the microemulsion system more stable.

A coenzyme Q10 microemulsion having a particle size $D_V(90)$ between 20 nm and 80 nm can be obtained by the aforesaid method.

<Ternary Phase Diagram of Microemulsion Area in Microemulsion>

The ternary phase diagram is one of the common methods to study the relationship between the distribution ratios of various components in a microemulsion. Generally, the three phases in a microemulsion are emulsifier/co-emulsifier, oil phase (insoluble substances and polar organic substances), and pure water. When pure water was added dropwise to the mixture of emulsifier/co-emulsifier and oil phase by Shah method, the system gradually changes from turbid to clear and then from clear to turbid with the increase of water quantity. The ratio data of the respective components at the two changes are recorded to form a ternary phase diagram, and then the microemulsion area of this system can be determined, and the optimal ratio of the components is further selected and determined in the microemulsion area according to the required performance.

From the magnitude of the microemulsion area, the water capacity of the system can be known. The larger the microemulsion area is, the more the microemulsion can maintain the microemulsion state after dilution in downstream uses, and the more it can remain stable and present a clear and transparent state in an extreme temperature environment, especially, it is not liable to precipitate at low temperature and not liable to be turbid at high temperature.

<Uses>

The coenzyme Q10 microemulsion of the present disclosure can be used in the pharmaceutical, cosmetic and food fields, and is particularly suitable for beverages and oral liquids.

The preparation process of microemulsion in the prior art is complicated and requires high-speed shearing, homogenization, and ultrasonication to achieve a particle size of less than 100 nm, and the resulting microemulsion has poor stability in extreme temperature environments (e.g., low temperature (−30° C. to −10° C.) and high temperature (100° C. to 130° C.)). In addition, the coenzyme Q10 microemulsion is also less used in the food field, and problems such as turbidity and demulsification will occur when the microemulsion is diluted into oral liquids.

In the present disclosure, by compounding specific emulsifiers and keeping the mixed components at a specific temperature, the preparation process can be simplified, and a microemulsion having a particle size $D_V(90)$ between 20 nm and 80 nm can be obtained. The microemulsion is clear and transparent and free of demulsification, and has high bioavailability, which can meet the needs of the pharmaceutical, cosmetic and food performance, and even meet the needs of oral liquid preparation under harsh conditions.

The method for detecting the performance of the coenzyme Q10 microemulsion of the present disclosure is described below.

<Test of Particle Size $D_V(90)$>

The microemulsion sample is diluted with distilled water at a ratio of 1:20 and gently shaken to form a clear microemulsion. Then, the particle size distribution of the emulsion is measured by MASTERSIZER 3000 laser particle size distribution instrument (purchased from Malvern Company, UK) at 25° C.

<Test of Clarification Transparency>

The clarification transparency test is also called demulsification test, and the type method is usually used to test clarification transparency.

The coenzyme Q10 microemulsion is quickly poured into a transparency meter barrel, and an inspector observes vertically downward from the barrel mouth of the transparency meter, and slowly releases the microemulsion just to a height of the microemulsion where the type at the bottom can be clearly recognized. The height of the microemulsion is the transparency of the coenzyme Q10 microemulsion, which is generally more than 30 cm to be transparent. The measurement is repeated for 3 times, and the results are averaged.

<Test of Stability>

Microemulsion samples and coenzyme Q10 raw material are placed in the conditions of irradiation at 4500 Lx light intensity, oxygen filling (25° C.) and 60° C. (incubator) for 15 days, respectively, for experiments. In these experiments, samples are taken on day 0, day 5, day 10 and day 15, respectively, and the content of coenzyme Q10 is determined by HPLC, to investigate the effects of light, oxygen and temperature on the labeled content (%) of coenzyme Q10 and the appearance.

<Test of Stability in Extreme Temperature Environments>

Low temperature: a microemulsion sample is placed in a medical refrigerator at −20° C. for 15 days, and the sample is taken on day 0, day 5, day 10 and day 15, respectively, and the content of coenzyme Q10 is determined by HPLC, to investigate the effects of a low temperature environment on the labeled content (%) and the appearance of coenzyme Q10.

High temperature: a microemulsion sample is stored in a thermostat at 120° C. for 0 minute, 10 minutes, 15 minutes and 30 minutes, and the sample is taken for the determination of the content of coenzyme Q10 by HPLC, to investigate the effects of high temperature environment on the labeled content (%) and the appearance of coenzyme Q10.

<Test of Bioavailability>

Preparation of coenzyme Q10 raw material sample solution: 0.1 g of coenzyme Q10 crystal is accurately weighed and dissolved in 100 mL of diethylene glycol monoethyl ether solution, as a raw material sample.

Microemulsion samples of Examples 1 to 6, coded as Sample 1, Sample 2, Sample 3, Sample 4, Sample 5 and Sample 6, are selected to conduct animal experiments.

Experimental conditions: the temperature of the laboratory feeding environment is 25±3° C., the relative humidity is 55% to 70%, the animals are free to drink water and eat food (deionized water and standard feed) every day, and they are fasted for 12 hours before the experiment but drink water freely.

Experimental animals and grouping: seventy 8-week-old healthy SPF-grade male SD rats, provided by Hubei Experimental Animal Research Center, weighing from 220 g to 230 g.

The rats are operated according to the international experimental guidelines for experimental animals, and every 10 rats fasted for 12 hours are divided into one group by a completely random design, totally seven groups.

Oral administration, sample collection and treatment: the rats are intragastrically administered with the same dose (15 mg/kg: coenzyme Q10 content) of microemulsion samples 1 to 6 and raw material samples, respectively. After administration, plasma is collected at 5 minutes, 15 minutes, 30 minutes, 1 hour, 3 hours, 6 hours, 10 hours and 15 hours, respectively, and put into anticoagulant centrifuge tubes containing heparin, mixed uniformly and then centrifuged to separate the plasma. After the treatment, the plasma concentration is detected by HPLC.

According to the results of the plasma concentration, statistical fitting analysis is carried out by using statistical analysis software, to calculate the plasma concentration. The results is expressed as mean value±standard deviation.

<Test of Coenzyme Q10 Content>

Refer to the test method of coenzyme Q10 content in Chinese Pharmacopoeia (2015 edition).

<Construction of Ternary Phase Diagram of Microemulsion Area>

The ternary phase diagram is constructed by the following method: control the temperature of the experiment at 50° C., and then dissolve a coenzyme Q10 crystal and an anti-crystallization agent in a carrier oil as an oil phase; uniformly mix emulsifiers (including a lipophilic emulsifier and an oleophilic emulsifier) and a co-emulsifier as an EM phase; weigh a certain amount of the oil phase and the EM phase respectively according to different mass ratios (1:1, 2:3, 1:2, 2:5, 3:7, 1:3, 2:7, 3:10, 1:4, 2:9, 5:12, 1:5, totally 12 groups), and mix them uniformly; slowly drop water into each group, and record the water consumption for each group when it changes from turbidity to clarification and when it changes from clarification to turbidity again; plot a ternary phase diagram according to the recorded data of oil phase, emulsifier/co-emulsifier and water quantity, using the mean values of two parallel experiments as the point values for the plot.

EXAMPLES

The present disclosure will be specifically described and illustrated by the following examples, but the present disclosure is not limited thereto.

Unless otherwise specified, the reagents and materials in the examples are all food-grade or pharmaceutical-grade, all of which are commercially available. Among them, coenzyme Q10 is from ZHEJIANG NHU CO., LTD., and the other raw materials are all commercially available.

Example 1

10% by mass of coenzyme Q10, 3% by mass of caprylic/capric triglyceride and 5% by mass of tocopherol acetate were dissolved by magnetic stirring in a water bath at 50° C. for 10 minutes to form an oil phase;

15% by mass of polyglycerol ricinoleate and 30% by mass of Tween-80 were added into the oil phase, and after each emulsifier was added, the mixture was magnetically stirred for 10 minutes;

After the oil phase was uniformly mixed, 5% by mass of ethanol was added, and after the oil phase was uniformly mixed by magnetic stirring, water was added dropwise while being magnetically stirred until the whole system became uniform and transparent. The system was stirred for 0.5 hour after the dropping and kept at 90° C. for 0.5 hour.

The coenzyme Q10 microemulsion of the present disclosure could be prepared by the aforesaid method, and the particle size $D_V(90)$ thereof is shown in Table 1.

Example 2 to Example 6

Coenzyme Q10 microemulsion was prepared according to the formulae shown in Table 1 in the same way as in Example 1, the content (% by mass) of the components was based on the total amount of the coenzyme Q10 microemulsion, the holding temperature changed within a range of 90° C. to 120° C. and the holding time changed within the range of 0.5 hour to 1 hour. The particle size $D_V(90)$ of the prepared microemulsion is shown in Table 1.

TABLE 1

| Formula | Example 1 | Example 2 | Example 3 | Example 4 | Example 5 | Example 6 |
|---|---|---|---|---|---|---|
| Coenzyme Q10 | 10 | 1 | 20 | 7 | 5 | 8 |
| Carrier oil | 2 caprylic/ capric triglyceride | 8 diethylene glycol monoethyl ether | 10 glycerol polyether | 1 soybean phospholipid | 20 olive oil | 5 (95% by mass of caprylic/capric triglyceride, 5% by mass of diethylene glycol monoethyl ether) |

TABLE 1-continued

| Formula | Example 1 | Example 2 | Example 3 | Example 4 | Example 5 | Example 6 |
|---|---|---|---|---|---|---|
| anti-crystallization agent | 5 tocopherol acetate Tocopherol acetate | 0.5 povidone K30 | 2 (80% by mass of povidone K12, 20% by mass of THL-17) | 10 (80% by mass of tocopherol, 20% by mass of THL-15) | 5 medium-chain triglyceride | 5 (80% by mass of tocopherol, 20% by mass of trihydroxy-stearin) |
| Lipophilic emulsifier | 15 polyglycerol ricinoleate | 2 polyglycerol ricinoleate | 5 polyglycerol ricinoleate | 10 polyglycerol ricinoleate | 15 Polyglycerol ricinoleate | 12 polyglycerol ricinoleate |
| Hydrophilic emulsifier | 24 Tween-80 | 15 (65% by mass of Tween-20, 35% by mass of Tween-60) | 17 (45% by mass of Tween-20, 35% by mass of Tween-60, 20% by mass of polyoxyethylene hydrogenated castor oil) | 30 (85% by mass of Tween-80, 15% by mass of polyoxyethylene hydrogenated castor oil) | 15 Polyoxyethylene hydrogenated castor oil | 15 Tween-60 |
| Co-emulsifier | 5 Ethanol | 9 Sorbitol | 12 Glycerol | 10 Polyethylene glycol-400 | 7 Polyethylene glycol-800 | 25 (95% by mass of sorbitol, 5% by mass of ethanol) |
| Water | 39 | 64.5 | 34 | 32 | 33 | 30 |
| Holding temperature (° C.) | 90 | 110 | 100 | 90 | 90 | 120 |
| Holding time (hour) | 0.5 | 0.6 | 0.5 | 1 | 0.5 | 0.5 |
| $D_V(90)$ (nm) | 75 | 62 | 45 | 47 | 73 | 60 |

According to the data in Table 1, coenzyme Q10 microemulsion could be obtained according to the formulae of Example 1 to Example 6, and the particle size $D_V(90)$ thereof was between 20 nm and 80 nm.

Comparative Example 1 to Comparative Example 4

Coenzyme Q10 microemulsions of Comparative Example 1 to Comparative Example 4 were prepared according to the formulae and the heat preservation conditions shown in Table 2 below in the same way as in Example 1, and the particle size $D_V(90)$ thereof was measured meanwhile.

In view of the data in Table 2, even though the other components, the holding temperature and holding time in Comparative Example 1 to Comparative Example 4 were the same as those in Example 1, the particle sizes of the coenzyme Q10 microemulsions prepared were relatively high due to the addition of only one lipophilic emulsifier or hydrophilic emulsifier. The experimental results show that coenzyme Q10 microemulsion having a particle size $D_V(90)$ between 20 nm and 80 n can be prepared only by combining specific emulsifiers in specific ratios.

TABLE 2

| Formula | Comparative Example 1 | Comparative Example 2 | Comparative Example 3 | Comparative Example 4 |
|---|---|---|---|---|
| Coenzyme Q10 | 10 | 10 | 10 | 10 |
| Carrier oil | 2 caprylic/ capric triglyceride | 2 caprylic/ capric triglyceride | 2 caprylic/ capric triglyceride | 2 caprylic/ capric triglyceride |
| Anti-crystallization agent | 5 Tocopherol acetate | 5 Tocopherol acetate | 5 Tocopherol acetate | 5 Tocopherol acetate |
| Emulsifier | 39 (95% by mass of D-α-tocopherol polyethylene glycol succinate (TPGS), 5% by mass of poloxamer) | 39 (70% by mass of Tween-80, 30% by mass of glyceryl monostearate) | 39 (25% by mass of Span-60, 75% by mass of Tween-60) | 39 (80% by mass of Tween-20, 20% by mass of sucrose ester) |
| Co-emulsifier | 5 Ethanol | 5 Ethanol | 5 Ethanol | 5 Ethanol |
| Water | 39 | 39 | 39 | 39 |
| Holding temperature (° C.) | 90 | 90 | 90 | 90 |
| Holding time (hour) | 0.5 | 0.5 | 0.5 | 0.5 |
| $D_V(90)$ (nm) | 180 | 175 | 130 | 95 |

Comparative Example 5 to Comparative Example 10 and Comparative Example 11 to Comparative Example 16

Coenzyme Q10 microemulsions of Comparative Example 5 to Comparative Example 10 and Comparative Example 11 to Comparative Example 16 were prepared according to the holding temperature and holding time shown in Tables 3 and 4 below in the same way as in Example 1, and the particle size $D_V(90)$ of the microemulsions was measured meanwhile.

TABLE 3

| Formula | Comparative Example 5 | Comparative Example 6 | Comparative Example 7 | Comparative Example 8 | Comparative Example 9 | Comparative Example 10 |
|---|---|---|---|---|---|---|
| Coenzyme Q10 | 10 | 10 | 10 | 10 | 10 | 10 |
| Carrier oil | 2 caprylic/ capric triglyceride | 2 caprylic/ capric triglyceride | 2 caprylic/ capric triglyceride | 2 caprylic/ capric triglyceridee | 2 caprylic/ capric triglyceride | 2 caprylic/ capric triglyceride |
| Anti-crystallization agent | 5 Tocopherol acetate | 5 Tocopherol acetate | 5 Tocopherol acetate | 5 Tocopherol acetate | 5 Tocopherol acetate | 5 Tocopherol acetate |
| Lipophilic emulsifier | 15 polyglycerol ricinoleate | 15 polyglycerol ricinoleate | 15 polyglycerol ricinoleate | 15 polyglycerol ricinoleate | 15 polyglycerol ricinoleate | 15 polyglycerol ricinoleate |
| Hydrophilic emulsifier | 24 Tween-80 | 24 Tween-80 | 24 Tween-80 | 24 Tween-80 | 24 Tween-80 | 24 Tween-80 |
| Co-emulsifier | 5 Ethanol | 5 Ethanol | 5 Ethanol | 5 Ethanol | 5 Ethanol | 5 Ethanol |
| Water | 39 | 39 | 39 | 39 | 39 | 39 |
| Holding temperature (° C.) | 50 | 60 | 70 | 80 | 130 | 140 |
| Holding time (hour) | 0.5 | 0.5 | 0.5 | 0.5 | 0.5 | 0.5 |
| $D_V(90)$ (nm) | 110 | 185 | 105 | 95 | 195 | 205 |

TABLE 4

| Formula | Comparative Example 11 | Comparative Example 12 | Comparative Example 7 | Comparative Example 13 | Comparative Example 14 | Comparative Example 15 |
|---|---|---|---|---|---|---|
| Coenzyme Q10 | 10 | 10 | 10 | 10 | 10 | 10 |
| Carrier oil | 2 caprylic/ capric triglyceride | 2 caprylic/ capric triglyceride | 2 caprylic/ capric triglyceride | 2 caprylic/ capric triglyceride | 2 caprylic/ capric triglyceride | 2 caprylic/ capric triglyceride |
| Anti-crystallization agent | 5 Tocopherol acetate | 5 Tocopherol acetate | 5 Tocopherol acetate | 5 Tocopherol acetate | 5 Tocopherol acetate | 5 Tocopherol acetate |
| Lipophilic emulsifier | 15 polyglycerol ricinoleate | 15 polyglycerol ricinoleate | 15 polyglycerol ricinoleate | 15 polyglycerol ricinoleate | 15 polyglycerol ricinoleate | 15 polyglycerol ricinoleate |
| Hydrophilic emulsifier | 24 Tween-80 | 24 Tween-80 | 24 Tween-80 | 24 Tween-80 | 24 Tween-80 | 24 Tween-80 |
| Co-emulsifier | 5 Ethanol | 5 Ethanol | 5 Ethanol | 5 Ethanol | 5 Ethanol | 5 Ethanol |
| Water | 39 | 39 | 39 | 39 | 39 | 39 |
| Holding temperature (° C.) | 90 | 90 | 90 | 90 | 90 | 90 |
| Holding time (hour) | 0.2 | 0.3 | 0.4 | 1.2 | 1.5 | 1.8 |
| $D_V(90)$ (nm) | 285 | 250 | 260 | 195 | 265 | 358 |

As shown by Table 3 and Table 4, though the formula of the microemulsion was the same as that of Example 1, due to different holding temperatures and holding times, the particle size $D_V(90)$ of the microemulsion was affected, and the values thereof were all greater than 80 nm. The experimental results show that the holding temperature and holding time have great influence on the particle size of microemulsion. In order to obtain coenzyme Q10 microemulsion having a particle size $D_V(90)$ in the range of 20 nm to 80 nm, it is preferable to control the holding time in the range of 0.5 hour to 1 hour and control the holding temperature in the range of 90° C. to 120° C.

The present application also carried out clarification transparency test (demulsification test) and stability test on coenzyme Q10 microemulsion of Example 1 to Example 6, and investigated the effects of illumination (4500 Lx illumination), oxygen (oxygen filling, 25° C.) and temperature (60° C., incubator) on the stability of coenzyme Q10 microemulsion, which are shown in Table 5, Table 6 and Table 7, respectively.

TABLE 5

| Test item | Sample | | 0 day | 5 days | 10 days | 15 days |
|---|---|---|---|---|---|---|
| Labeled content of coenzyme Q10 (%) | microemulsion | Example 1 | 10.0 | 9.9 | 9.9 | 9.8 |
| | | Example 2 | 1.0 | 0.9 | 0.9 | 0.9 |
| | | Example 3 | 4.0 | 3.9 | 3.9 | 3.9 |
| | | Example 4 | 7.0 | 6.9 | 6.9 | 6.8 |
| | | Example 5 | 10.0 | 10.0 | 9.9 | 9.9 |
| | | Example 6 | 8.0 | 7.9 | 8.0 | 8.0 |
| | coenzyme Q10 raw material | | 99 | 95 | 93 | 88 |
| Appearance | microemulsion | Example 1 | clear and transparent | clear and transparent | clear and transparent | clear and transparent |
| | | Example 2 | clear and transparent | clear and transparent | clear and transparent | clear and transparent |
| | | Example 3 | clear and transparent | clear and transparent | clear and transparent | clear and transparent |
| | | Example 4 | clear and transparent | clear and transparent | clear and transparent | clear and transparent |
| | | Example 5 | clear and transparent | clear and transparent | clear and transparent | clear and transparent |
| | | Example 6 | clear and transparent | clear and transparent | clear and transparent | clear and transparent |
| | coenzyme Q10 raw material | | Yellow crystalline powder | Yellow crystalline powder | Yellow crystalline powder | Yellow crystalline powder |

TABLE 6

| Test item | Sample | | 0 day | 5 days | 10 days | 15 days |
|---|---|---|---|---|---|---|
| Labeled content of coenzyme Q10 (%) | Micro-emulsion | Example 1 | 10.0 | 10.0 | 9.9 | 9.9 |
| | | Example 2 | 1.0 | 0.9 | 0.9 | 0.9 |
| | | Example 3 | 4.0 | 4.0 | 3.9 | 3.9 |
| | | Example 4 | 7.0 | 6.9 | 6.9 | 6.9 |
| | | Example 5 | 10.0 | 10.0 | 9.9 | 9.9 |
| | | Example6 | 8.0 | 7.9 | 7.9 | 7.9 |
| | coenzyme Q10 raw material | | 99 | 97 | 95 | 90 |
| Appearance | Micro-emulsion | Example 1 | clear and transparent | clear and transparent | clear and transparent | clear and transparent |
| | | Example 2 | clear and transparent | clear and transparent | clear and transparent | clear and transparent |
| | | Example 3 | clear and transparent | clear and transparent | clear and transparent | clear and transparent |
| | | Example 4 | clear and transparent | clear and transparent | clear and transparent | clear and transparent |
| | | Example 5 | clear and transparent | clear and transparent | clear and transparent | clear and transparent |
| | | Example 6 | clear and transparent | clear and transparent | clear and transparent | clear and transparent |
| | coenzyme Q10 raw material | | Yellow crystalline powder | Yellow crystalline powder | Yellow crystalline powder | Yellow crystalline powder |

TABLE 7

| Test item | Sample | | 0 day | 5 days | 10 days | 15 days |
|---|---|---|---|---|---|---|
| Labeled content of coenzyme Q10 (%) | Micro-emulsion | Example 1 | 10.0 | 9.9 | 9.9 | 9.9 |
| | | Example 2 | 1.0 | 0.9 | 0.9 | 0.8 |
| | | Example 3 | 4.0 | 3.9 | 3.9 | 3.9 |
| | | Example 4 | 7.0 | 6.9 | 6.9 | 6.8 |
| | | Example 5 | 10.0 | 10.0 | 9.9 | 9.9 |
| | | Example 6 | 8.0 | 8.0 | 7.9 | 7.9 |
| | coenzyme Q10 raw material | | 99 | 97 | 95 | 92 |
| Appearance | Micro-emulsion | Example 1 | clear and transparent | clear and transparent | clear and transparent | clear and transparent |
| | | Example 2 | clear and transparent | clear and transparent | clear and transparent | clear and transparent |
| | | Example 3 | clear and transparent | clear and transparent | clear and transparent | clear and transparent |
| | | Example 4 | clear and transparent | clear and transparent | clear and transparent | clear and transparent |

TABLE 7-continued

| Test item | Sample | 0 day | 5 days | 10 days | 15 days |
|---|---|---|---|---|---|
| | Example 5 | clear and transparent | clear and transparent | clear and transparent | clear and transparent |
| | Example 6 | clear and transparent | clear and transparent | clear and transparent | clear and transparent |
| | coenzyme Q10 raw material | Yellow crystalline powder | Yellow crystalline powder | Yellow crystalline powder | Yellow crystalline powder |

As shown by Table 5 to Table 7, when the coenzyme Q10 microemulsions of Example 1 to Example 6 were exposed to illumination (4500 Lx illumination), oxygen (oxygen filling, 25° C.) and high temperature (60° C., incubator), the labeled content and the appearance of coenzyme Q10 did not change significantly. Specifically, the measured results of the labeled content of coenzyme Q10 showed little change on day 5, day 10 and day 15 and were more stable than the labeled content of coenzyme Q10 in the raw material. Besides, the appearance of the microemulsion was clear and transparent, and there is no turbidity and demulsification. Therefore, the coenzyme Q10 microemulsion of the present disclosure has good stability to illumination, oxygen and temperature, and can prolong the shelf life of products.

Besides, the present application also carried out performance experiments on coenzyme Q10 microemulsions of Example 1 to Example 6, Comparative Example 1 to Comparative Example 4 at low temperature (−20° C.) and high temperature (120° C.) to test the changes of the labeled content and the appearance of coenzyme Q10, wherein the experimental results at low temperature (−20° C.) are shown in Table 8, and those at high temperature (120° C.) are shown in Table 9.

TABLE 8

| Test item | Sample | 0 day | 5 days | 10 days | 15 days |
|---|---|---|---|---|---|
| Labeled content of coenzyme Q10 (%) | Example 1 | 10.0 | 10 | 10 | 10 |
| | Example 2 | 1.0 | 1.0 | 1.0 | 1.0 |
| | Example 3 | 4.0 | 4.0 | 4.0 | 4.0 |
| | Example 4 | 7.0 | 7.0 | 7.0 | 7.0 |
| | Example 5 | 10.0 | 10.0 | 10.0 | 10.0 |
| | Example 6 | 8.0 | 8.0 | 8.0 | 8.0 |
| | Comparative Example 1 | 10.0 | 10.0 | 10.0 | 10.0 |
| | Comparative Example 2 | 10.0 | 10.0 | 10.0 | 10.0 |
| | Comparative Example 3 | 10.0 | 10.0 | 10.0 | 10.0 |
| | Comparative Example 4 | 10.0 | 10.0 | 10.0 | 10.0 |
| Appearance | Example 1 | clear and transparent | clear and transparent | clear and transparent | clear and transparent |
| | Example 2 | clear and transparent | clear and transparent | clear and transparent | clear and transparent |
| | Example 3 | clear and transparent | clear and transparent | clear and transparent | clear and transparent |
| | Example 4 | clear and transparent | clear and transparent | clear and transparent | clear and transparent |
| | Example 5 | clear and transparent | clear and transparent | clear and transparent | clear and transparent |
| | Example 6 | clear and transparent | clear and transparent | clear and transparent | clear and transparent |
| | Comparative Example 1 | clear and translucent | Turbid and crystallized | Turbid and crystallized | Turbid and crystallized |
| | Comparative Example 2 | clear and translucent | Turbid and crystallized | Turbid and crystallized | Turbid and crystallized |
| | Comparative Example 3 | clear and translucent | Turbid and crystallized | Turbid and crystallized | Turbid and crystallized |
| | Comparative Example 4 | clear and translucent | Turbid and crystallized | Turbid and crystallized | Turbid and crystallized |

TABLE 9

| Test item | Sample | 0 min | 5 min | 10 min | 15 min | 30 min |
|---|---|---|---|---|---|---|
| Labeled content of coenzyme Q10 (%) | Example 1 | 10.0 | 10 | 10 | 10 | 10 |
| | Example 2 | 1.0 | 1.0 | 1.0 | 1.0 | 1.0 |
| | Example 3 | 4.0 | 4.0 | 4.0 | 4.0 | 4.0 |
| | Example 4 | 7.0 | 7.0 | 7.0 | 7.0 | 7.0 |
| | Example 5 | 10.0 | 10.0 | 10.0 | 10.0 | 10.0 |

TABLE 9-continued

| Test item | Sample | 0 min | 5 min | 10 min | 15 min | 30 min |
|---|---|---|---|---|---|---|
| | Example 6 | 8.0 | 8.0 | 8.0 | 8.0 | 8.0 |
| | Comparative Example 1 | 10.0 | 10.0 | 9.9 | 9.9 | 9.8 |
| | Comparative Example 2 | 10.0 | 10.0 | 9.9 | 9.9 | 9.8 |
| | Comparative Example 3 | 10.0 | 10.0 | 9.8 | 9.8 | 9.7 |
| | Comparative Example 4 | 10.0 | 10.0 | 10.0 | 9.9 | 9.8 |
| Appearance | Example 1 | clear and transparent | clear and transparent | clear and transparent | clear and transparent | clear and transparent |
| | Example 2 | clear and transparent | clear and transparent | clear and transparent | clear and transparent | clear and transparent |
| | Example 3 | clear and transparent | clear and transparent | clear and transparent | clear and transparent | clear and transparent |
| | Example 4 | clear and transparent | clear and transparent | clear and transparent | clear and transparent | clear and transparent |
| | Example 5 | clear and transparent | clear and transparent | clear and transparent | clear and transparent | clear and transparent |
| | Example 6 | clear and transparent | clear and transparent | clear and transparent | clear and transparent | clear and transparent |
| | Comparative Example 1 | clear and translucent | clear and translucent | turbid | completely turbid | completely turbid |
| | Comparative Example 2 | clear and translucent | clear and translucent | turbid | completely turbid | completely turbid |
| | Comparative Example 3 | clear and translucent | clear and translucent | turbid | completely turbid | completely turbid |
| | Comparative Example 4 | clear and translucent | clear and translucent | turbid | completely turbid | completely turbid |

As shown by Table 8 and Table 9, when the coenzyme Q10 microemulsions of Example 1 to Example 6 were at a low temperature (−20° C.) and a high temperature (120° C.), the labeled content and the appearance of coenzyme Q10 did not change significantly, and the appearance of the microemulsions was clear and transparent, without turbidity and demulsification. In contrast, the coenzyme Q10 microemulsions of Comparative Example 1 to Comparative Example 4 were not stable in a low-temperature environment, and coenzyme Q10 crystals precipitated in a short time, which led to demulsification of the microemulsion system. Besides, the appearance of Comparative Example 1 to Comparative Example 4 was also unstable at high temperature. With the extension of storage time, the microemulsion became completely turbid and the microemulsion system was destroyed. The data in the tables show that the microemulsion of the present disclosure has excellent stability in extreme temperature environments and can meet the needs of microemulsion in subsequent uses.

In order to investigate the bioavailability of coenzyme Q10 microemulsion, the present application carried out experiments in this respect on coenzyme Q100 microemulsions of Example 1 to Example 6. Table 10 shows the results of the average plasma concentration-time (mean±SD, n=10) (μg/L) of rats after oral administration of the sample.

TABLE 10

| | Samples | | | | | | Raw |
|---|---|---|---|---|---|---|---|
| Sampling time | Example 1 | Example 2 | Example 3 | Example 4 | Example 5 | Example 6 | materials |
| 5 minutes | 123.1 ± 1.11 | 118.1 ± 1.09 | 108.1 ± 1.39 | 102.7 ± 1.11 | 110.1 ± 0.56 | 109.8 ± 1.42 | 12.1 ± 0.42 |
| 15 minutes | 166.3 ± 1.31 | 151.3 ± 1.21 | 142.3 ± 1.12 | 142.7 ± 1.30 | 156.8 ± 1.26 | 141.3 ± 1.41 | 21.3 ± 1.01 |
| 30 minutes | 233.4 ± 2.41 | 241.3 ± 2.37 | 206.5 ± 2.15 | 211.7 ± 2.20 | 239.5 ± 2.67 | 231.3 ± 2.45 | 49.3 ± 1.37 |
| 1 hour | 423.5 ± 2.94 | 402.9 ± 3.04 | 419.2 ± 2.84 | 395.4 ± 3.05 | 396.9 ± 3.52 | 409.5 ± 3.24 | 93.0 ± 1.15 |
| 3 hours | 317.4 ± 2.36 | 304.4 ± 2.62 | 282.4 ± 1.92 | 296.6 ± 2.35 | 314.4 ± 2.85 | 309.4 ± 2.65 | 110.4 ± 1.62 |
| 6 hours | 193.6 ± 1.78 | 188.3 ± 1.55 | 173.9 ± 1.23 | 184.6 ± 1.34 | 198.3 ± 1.88 | 188.9 ± 1.35 | 83.3 ± 1.05 |
| 10 hours | 156.7 ± 1.33 | 147.6 ± 1.24 | 126.3 ± 1.03 | 115.8 ± 1.14 | 157.6 ± 1.54 | 151.6 ± 1.28 | 37.6 ± 1.24 |
| 15 hours | 103.3 ± 0.99 | 107.4 ± 0.69 | 98.8 ± 0.38 | 109.2 ± 0.85 | 107.3 ± 0.52 | 105.5 ± 0.60 | 11.5 ± 0.22 |
| $D_V(90)$(nm) | 75 | 62 | 45 | 47 | 73 | 60 | 75000 |

As shown by the data in Table 10, after the administration of oral liquid, the microemulsions of Example 1 to Example 6 had statistically significantly higher peak concentration $C_{max}$($P<0.05$) and significantly higher AUC value than the raw materials, and the fluctuation of the peak concentration was also smaller than that of the raw materials. The results show that coenzyme Q10 microemulsion has high bioavailability, can be absorbed quickly in rats, and can reach a high plasma concentration, and the drug safety is also high. Moreover, because the particle size $D_V(90)$ of the microemulsion is between 20 nm and 80 nm, the smaller particle size can improve the uniformity of drug absorption and is beneficial to drug absorption.

In addition, by using the microemulsion components of Example 1, and Comparative Example 1 to Comparative Example 3 at different component ratios, respectively, the present application also plots ternary phase diagrams according to the above-mentioned method, which are shown in FIG. 1 to FIG. 4, respectively. The specific formulae of Example 1, and Comparative Example 1 to Comparative Example 3 are the values of certain points in the microemulsion areas of FIG. 1 to FIG. 4.

As can be seen, the microemulsion area shown in FIG. 1 is relatively large, which indicates that the microemulsion system in Example 1 has a large water capacity, so it can still maintain the microemulsion state after being diluted in downstream uses, and the microemulsion is more stable in extreme temperature environments, shows a clear and transparent state, and is not liable to precipitate at low temperature and not liable to be turbid at high temperature. In contrast, the microemulsion systems in FIG. 2 to FIG. 4 for Comparative Example 1 to Comparative Example 3 have small microemulsion areas, which indicate that these microemulsion systems have a small water capacity, and the microemulsion appears unstable states such as precipitation or turbidity in extreme temperature environments.

INDUSTRIAL UTILITY

The present disclosure provides a method for preparing the coenzyme Q10 microemulsion, which is simple in equipment, low in cost and easy in operation. The microemulsion prepared by this method has a particle size $D_V(90)$ of between 20 nm and 80 nm, and is clear, transparent, free of demulsification and high in bioavailability, can be stably stored for a long time at normal temperatures and in extreme temperature environments. The microemulsion prepared in the present disclosure is suitable for the pharmaceutical, cosmetic and food fields, especially for products such as beverages and oral liquids.

What is claimed is:

1. A coenzyme Q10 microemulsion comprising, based on a total amount of the coenzyme Q10 microemulsion, 1% to 20% by mass of coenzyme Q10, 1% to 20% by mass of a carrier oil, 0.5% to 10% by mass of an anti-crystallization agent, 2% to 15% by mass of a lipophilic emulsifier, 15% to 30% by mass of a hydrophilic emulsifier, 5% to 25% by mass of a co-emulsifier, and 30% to 65% by mass of water, said coenzyme Q10 microemulsion having a particle size Dv(90) of 20 nm to 80 nm, wherein the lipophilic emulsifier includes polyglycerol ricinoleate, wherein the hydrophilic emulsifier includes a polyoxyethylene ether-based emulsifier, wherein the polyoxyethylene ether-based emulsifier is at least one selected from the group consisting of polyoxyethylene sorbitan oleate, polyoxyethylene sorbitan stearate, polyoxyethylene sorbitan laurate and polyoxyethylene hydrogenated castor oil, wherein the carrier oil is at least one selected from the group consisting of diethylene glycol monoethyl ether, glycerol polyether, soybean phospholipid and olive oil.

2. The coenzyme Q10 microemulsion according to claim 1, wherein the co-emulsifier is at least one selected from the group consisting of glycerol, sorbitol, ethanol, polyethylene glycol-400 and polyethylene glycol-800.

3. The coenzyme Q10 microemulsion according to claim 1, wherein the anti-crystallization agent is at least one selected from the group consisting of tocopherol acetate, tocopherol, trihydroxystearin, medium-chain triglyceride, povidone K30, povidone K12 and polyglycerol fatty acid ester.

4. A method for preparing the coenzyme Q10 microemulsion according to claim 1, comprising steps of:

forming an oil phase using a coenzyme Q10, a carrier oil and an anti-crystallization agent;

adding a lipophilic emulsifier and a hydrophilic emulsifier into the oil phase;

further adding a co-emulsifier after the oil phase is uniformly mixed, stirring and mixing uniformly, and then adding water dropwise, followed by stirring until the whole system becomes uniform and transparent, keeping the temperature at 90° C. to 120° C. for 0.5 hour to 1 hour, thereby obtaining the coenzyme Q10 microemulsion.

5. A method for preparing pharmaceuticals, cosmetics or food, comprising utilizing the coenzyme Q10 microemulsion according to claim 1.

6. A method for preparing a beverage or an oral liquid, comprising utilizing the coenzyme Q10 microemulsion according to claim 1.

* * * * *